United States Patent [19]

Krumbholz et al.

[11] Patent Number: 5,071,530

[45] Date of Patent: Dec. 10, 1991

[54] METHOD OF MANUFACTURING LACTULOSE

[75] Inventors: Rudolf E. Krumbholz; Michael G. Dorscheid, both of Weesp, Netherlands

[73] Assignee: Duphar International Research B.V., Weesp, Netherlands

[21] Appl. No.: 451,782

[22] Filed: Dec. 18, 1989

[30] Foreign Application Priority Data

Dec. 21, 1988 [DE] Fed. Rep. of Germany ....... 3843022

[51] Int. Cl.$^5$ .......................... C07H 3/04; C07C 47/18
[52] U.S. Cl. ............................... 204/182.3; 204/182.6; 127/30; 127/40; 127/46.2; 127/54; 536/125
[58] Field of Search .................... 204/182.6, 182.3; 127/30, 46.2, 46.1, 54, 40; 536/125, 127

[56] References Cited

U.S. PATENT DOCUMENTS

| | | | |
|---|---|---|---|
| 3,505,309 | 4/1970 | Carubelli | 127/42 |
| 3,546,206 | 12/1970 | Guth et al. | 127/42 |
| 3,715,235 | 2/1973 | Moebes et al. | 127/46.2 |
| 3,850,905 | 11/1974 | Tumerman | 127/54 |
| 4,226,977 | 10/1980 | Neuzil et al. | 536/127 |
| 4,264,763 | 4/1981 | Gasparotti | 536/18.5 |
| 4,273,922 | 6/1981 | Hicks | 127/30 |
| 4,394,178 | 7/1983 | Chao et al. | 536/127 |
| 4,536,221 | 8/1985 | Carobbi et al. | 127/30 |
| 4,555,271 | 11/1985 | Carobbi et al. | 127/46.2 |
| 4,565,582 | 1/1986 | Filippini et al. | 127/46.1 |

FOREIGN PATENT DOCUMENTS 035267 3/1983 Hungary.
47-39545 12/1972 Japan.
77000091 1/1977 Japan.

Primary Examiner—John Niebling
Assistant Examiner—Arun S. Phasge
Attorney, Agent, or Firm—Stevens, Davis, Miller & Mosher

[57] ABSTRACT

For the manufacture of lactulose, an alkaline aqueous solution of lactose and borax is prepared and heated at a temperature above 80° C. The lactulose is separated from the resulting conversion products. Apart from the borax, no alkalizing material is added to the solution. The conversion is carried out at pH 8.3.

In order to maintain the sodium ions in the production cycle, the borax may be manufactured in an aqueous solution of boric acid and already simultaneously with the lactose, while the sodium ions are transferred from the solution of the conversion products in the solution of the boric acid by electrodialysis.

Alternatively the sodium ions may also be removed from the solution of the conversion products as readily as possible by means of a weakly acid ion exchanger and only thereafter by means of a more strongly acid ion exchanger.

The weakly acid ion exchanger is regenerated with boric acid so that borax is formed again.

10 Claims, No Drawings

METHOD OF MANUFACTURING LACTULOSE

The invention relates to a method of manufacturing lactulose, in which an alkaline aqueous solution of lactulose and borax is prepared and heated at a temperature above 80° C. and the lactulose is separated from the resulting conversion products.

This method is known from, for example, Chemical Abstracts 86: 173382h. Since conversion requires an alkaline medium, sodium hydroxyde solution is additionally added. The yield of the method is comparatively high; the boric acid forms with the lactulose a complex which shifts the equilibrium away from the lactose. Furthermore, galactose, tagatose, other sugars, organic acids and dyes are formed from the lactose as conversion products.

It is an object of the invention to provide a method of manufacturing lactulose which is similarly economical, but which is ecologically more sound.

According to the invention this object is achieved in that the method mentioned hereinbefore can also be carried out when, apart from borax, substantially no alkalising material is added to the solution.

The sewage load with alkali salts—which after removing the alkali ions by ion exchangers are formed in the regeneration of the ion exchangers —is thus considerably reduced.

As a further step in this direction the method enables a recycling of the sodium ions according to two modified embodiments of the invention:

One embodiment consists in that the borax is manufactured in an aqueous solution of boric acid, preferably already simultaneously with the lactose, in that the sodium ions are transferred from the solution of the conversion products into the solution of the boric acid by electrodialysis.

In this manner a complete recycling of the sodium ions is possible.

For this purpose only two compartments separated by a cation exchanging membrane are necessary. One compartment is the cathode compartment and the boric acid solution, preferably boric acid lactose solution, flows through it. The solution of the conversion products flows through the other compartment which is the anode compartment. Under the applied voltage the sodium ions move into the first compartment so that a borax solution is formed in the said compartment.

The other embodiment consists in that the sodium ions are removed from the solution of the conversion products substantially as completely as possible by means of a weakly acid ion exchanger and only thereafter by means of a more strongly acid ion exchanger, whereas the weakly acid ion exchanger is preferably at least partly regenerated with boric acid and the borax then formed is re-used, at least partly.

In other words: as long as the sodium ion concentration in the solution of the conversion products is so high that a weakly acid ion exchanger also binds the sodium ions, such an ion exchanger will be used. A strongly acid ion exchanger will then be used only for the complete separation of the sodium ions from the solution. As a result of the preferred regeneration of the weakly acid ion exchanger with boric acid, the sodium ions bound by same will remain in the production cycle. Only the rest is removed to the sewage. However, also in the case in which the weakly acid ion exchanger is not regenerated with boric acid, its use is of advantage. Anyhow it may be regenerated with a weaker acid which is better from an ecological point of view. Carbonic acid, for example, is ecologically sound.

As a further embodiment of the method according to the invention it is suggested that, for separating the lactulose, the solution of the reaction products after separating the sodium ions, prior to or after the separation of the borate ions, preferably after evaporating to 15 to 20% dry material, is passed through a long container packed with a weakly basic ion exchanger as a chromatography column, preferably at 30° to 60° C., water being used as an eluent.

This new use of an ion exchanger leads to an excellent separation of the lactulose, but also of the galactose from the mixture of the reaction products. A lactulose can be obtained having a degree of purity of over 99%, which up till now has been possible on an industrial scale only at incommensurably higher cost.

As the last step of the method and the modified embodiment of the invention it is finally suggested for the manufacture of lactulose powder to add, preferably spray, a concentrated lactulose solution having a purity of at least 90% lactulose, based on dry material, to a lactulose powder which is kept in motion, preferably stirred, so slowly and to distribute it therein so rapidly and finely that the lactulose solution always forms only a thin film on the surface of the powder particles from which the solid material grows on the powder particles.

It is known that it is not possible to crystallise lactulose simply by concentration from an aqueous solution.

Methanol or another organic solvent has so far been added for the manufacture of lactulose powder, in which solvent the lactulose has a smaller solubility and precipitates. The mechanically separated and dried powder then is always contaminated with a residue of the solvent.

The suggested new method on the contrary enables the manufacture of a free-flowing, only weakly hygroscopic lactulose powder of high purity.

Decisive for this method is the slow addition and immediate distribution and spreading of the lactulose syrup on the grains to form a thin film. Even only local accumulations of the syrup are to be avoided. Above all, already crystalline material must not dissolve again in the syrup. Suitable for this purpose are, for example, spray-driers, paddle driers and other hot-air driers having a stirring mechanism.

The above suggestions for the formation of a borax solution by electrodialysis, the removal of sodium ions from the solution of the conversion products by means of a weakly acid ion exchanger, the separation of the lactulose by means of a weakly basic ion exchanger as a chromatography column, and the manufacture of a lactulose powder are in combination advantageous within the scope of the present invention, but each of these measures may also be used separately to get certain advantages.

EXAMPLE 175 kg of lactose-monohydrate, 46.3 kg of borax and 800 kg of de-ionised water are heated at 95° C. and kept at this temperature for 3 hours. A mixture of reaction products is formed which comprises substantially 74.2 kg of lactulose, 75.3 kg of lactose, 8.0 kg of galactose and 0.8 kg of tagatose. The resulting sugar mixture solution is passed over a weakly acid ion exchanger and subsequently over a strongly acid ion exchanger, so that the sodium ions originating from the borax are removed. The solution is then evaporated to 15% dry material.

The solution having this concentration is passed over a chromatography column consisting of a weakly basic ion exchanger.

In fact the column consists of a hollow cylinder having a diameter of approximately 90 cm and a height of 2 m. filled with 1000 l of the weakly basic ion exchange resin. 1000 l of the solution are added at a temperature between 40° and 60° C., to the column which was previously filled with water and subsequently replenished with water, at a flow rate of 1 to 2 bed volumes/hour.

The diagram hereinafter shows the achieved separation of the components of the solution. It appears that with only a small loss a nearly pure, lactulose fraction without other sugars can be obtained. The sharp separation of lactose and lactulose is particularly surprising.

The resulting lactulose solution is liberated from the boric acid in a boron-specific exchanger and is then evaporated to a content of 65% lactulose in, for example, a vacuum of 40 mbar. A marketable syrup is thus obtained.

However, the syrup may also be converted into a powder

For that purpose, for example, a steamheated paddle drier is used (De Dietrich SP 200), total capacity 200 l and useful contents 130 l, stirrer speed 10 rpm. 20 kg of lactulose powder are put into the container and totally 100 kg of syrup heated at 60° C. are drawn in at a flow rate of 2 l/hour. The whole is then dried for 30 minutes. 20 kg of the resulting powder remain as a sample for the next batch.

Instead of the addition of borax as described hereinbefore, the following method may be used:

175 kg of lactose-monohydrate, 30 kg of boric acid and 600 kg of de-ionised water are dissolved while stirring at approximately 45° C. and are passed over the described weakly acid ion exchanger which is loaded with the sodium ions. Elution is carried out with de-ionised water. The resulting solution which has regenerated the ion exchanger at least partly with the boric acid and has taken up the sodium ions, is adjusted by means of sodium hydroxide solution at pH 8.3 i.e. the pH-value of the above described lactose-borax solution.

The conversion then occurs as with the said solution.

We claim:

1. A method of manufacturing lactulose comprising the steps of (a) preparing an aqueous solution of lactose and borax, (b) reacting said components of this solution at a temperature of at least 80° C., and (c) substantially separating the lactulose from unconverted lactose and from the side products, wherein in step (a), apart from the borax, substantially no alkalizing material is added to the aqueous solution.

2. A method as claimed in claim 1, characterized in that the borax is manufactured in an aqueous solution of boric acid, and in that the sodium ions are transferred

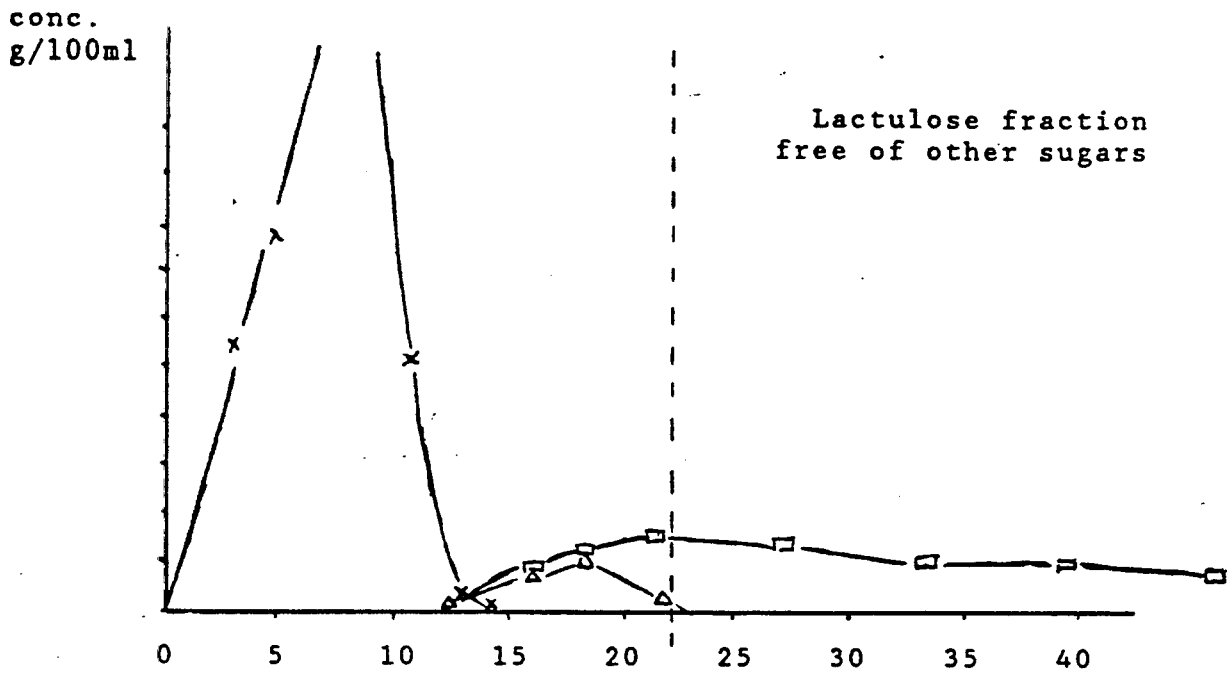

from the solution of the conversion products into the solution of the boric acid by electrodialysis.

3. A method as claimed in claim 2, wherein the borax is manufactured in an aqueous solution of boric acid and lactose.

4. A method as claimed in claim 1, wherein the solution of the conversion products is passed successively over a weakly acid ion exchanger and then a strongly acid ion exchanger.

5. A method as claimed in claim 4, characterized in that the weakly acid ion exchanger is regenerated at least partly with boric acid and that the borax formed during said regeneration is used at least partly in the initial preparation of the lactose/borax solution.

6. A method as claimed in claim 1, or 2, or 4, or 5, characterized in that for the separation of the lactulose the solution of the reaction products after separating the sodium ions, and prior to the separation of the borate ions, is passed through a long chromatography column filled with a weakly basic ion exchanger, water being used as an eluent.

7. A method as claimed in claim 1, or 2, or 4, or 5, characterized in that for the manufacture of lactulose powder, a concentrated lactulose solution having a purity of at least 90% lactulose based on dry material is added to a lactulose powder which is kept in motion, and is distributed therein so rapidly and finely that the lactulose solution always forms only a thin film on the surface of the powder particles.

8. Lactulose prepared according to a method as claimed in claim 1, or 2, or 4, or 5.

9. A method as claimed in claim 6, wherein the solution of the reaction products is evaporated to 15-20% dry material prior to passing same through the said chromatography column at 30° to 60°.

10. A method as claimed in claim 7, wherein the said concentrated lactulose solution is added to the said lactulose powder by spraying, while the powder is stirred.

* * * * *